US012642435B2

(12) United States Patent
Lai et al.

(10) Patent No.: US 12,642,435 B2
(45) Date of Patent: Jun. 2, 2026

(54) SYSTEM AND METHOD FOR TISSUE ANALYSIS USING REMOTE PPG

(71) Applicant: KONINKLIJKE PHILIPS N.V., Eindhoven (NL)

(72) Inventors: Marco Lai, Eindhoven (NL); Bernardus Hendrikus Wilhelmus Hendriks, Eindhoven (NL); Gerhardus Wilhelmus Lucassen, Eindhoven (NL); Marc Notten, Elsloo (NL); Nico Maris Adriaan De Wild, Eindhoven (NL); Frank Verbakel, Helmond (NL); Sergei Y. Shulepov, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 18/838,085

(22) PCT Filed: Feb. 15, 2023

(86) PCT No.: PCT/EP2023/053768
§ 371 (c)(1),
(2) Date: Aug. 13, 2024

(87) PCT Pub. No.: WO2023/156463
PCT Pub. Date: Aug. 24, 2023

(65) Prior Publication Data
US 2025/0143577 A1 May 8, 2025

(30) Foreign Application Priority Data

| Feb. 18, 2022 | (EP) | ................................... | 22157397 |
| Feb. 18, 2022 | (EP) | ................................... | 22157421 |
| Jan. 29, 2023 | (WO) | ................ | PCT/EP2023/052103 |

(51) Int. Cl.
| A61B 5/00 | (2006.01) |
| A61B 5/0295 | (2006.01) |
| G06T 7/00 | (2017.01) |

(52) U.S. Cl.
CPC .......... *A61B 5/0075* (2013.01); *A61B 5/0295* (2013.01); *G06T 7/0014* (2013.01); *G06T 2207/10036* (2013.01); *G06T 2207/30076* (2013.01)

(58) Field of Classification Search
CPC ............................ G06T 7/0012; G06T 7/0014
See application file for complete search history.

(56) References Cited

U.S. PATENT DOCUMENTS

| 6,512,807 B1 | 1/2003 | Pohlman |
| 2014/0148663 A1* | 5/2014 | Bresch ................. A61B 5/7225 |
| | | 600/407 |

(Continued)

FOREIGN PATENT DOCUMENTS

| CN | 108042107 A | 5/2018 |
| WO | 2015023990 A1 | 2/2015 |

OTHER PUBLICATIONS

International Search Report and Written Opinion of PCT/EP2023/053768, dated Mar. 30, 2023.

(Continued)

*Primary Examiner* — Carolyn A Pehlke

(57) ABSTRACT

A system and method for PPG analysis processes images to determine PPG signals from different image regions of the images and determine relative delays between the PPG signals for the different image regions. The time alignment between the PPG signals is improved so that a more accurate global PPG signal is obtained for the overall region of interest. In this way, PPG signals are realigned or partially realigned to provide an overall PPG signal with improved signal to noise ratio.

14 Claims, 13 Drawing Sheets

(56) References Cited

U.S. PATENT DOCUMENTS

| | | |
|---|---|---|
| 2014/0213910 A1 | 7/2014 | Durkin |
| 2014/0275880 A1 | 9/2014 | Verkruijsse |
| 2017/0055894 A1 | 3/2017 | Panasyuk |
| 2017/0079530 A1 | 3/2017 | Dimaio |
| 2017/0319114 A1 | 11/2017 | Kaestle |
| 2017/0354334 A1* | 12/2017 | Tarassenko ............ A61B 5/742 |
| 2019/0175030 A1 | 6/2019 | Verkruijsse |
| 2020/0138360 A1 | 5/2020 | Fan |
| 2021/0068687 A1 | 3/2021 | Tarniceriu |
| 2022/0354418 A1 | 11/2022 | Bourquin |
| 2022/0409144 A1 | 12/2022 | Priem |
| 2024/0041342 A1 | 2/2024 | Lai |

OTHER PUBLICATIONS

Zaunseder, Sebastian et al "Spatio-Temporal Analysis of Blood Perfusion by Imaging Photoplethysmography", Optical Diagnostics and Sensing XVII: Toward Point-Of-Care Diagnostics, Proc. of Spie, vol. 10501, 2018.

Lai, Marco et al "Perfusion Monitoring by Contactless Photoplethysmography Imaging", IEEE 16th International Symposium On Biomedical Imaging, Apr. 2019.

Lai, Marco et al "Evaluation of a Non-contact Photo-Plethysmographic Imaging (iPPG) System for Peripheral Arterial Disease Assessment", SPIE Medical Imaging, 2021.

Lai, Marco et al "Perfusion Monitoring by Non-Contact Photoplethysmorgraphic (PPG) Imaging", R-TN-2016/00448, 2017.

Pang, Zongguang et al "Accurate Measurement of Imaging Photoplethysmographic Signals based Camera using Weighted Average", International Conf. on Optical Instruments and Technology: Optoelectronic Imaging/Spectroscopy and Signal Processing Technology, Proc. of SPIE, vol. 10620, 2018.

* cited by examiner

10 a)

b)

a)

c)

SYSTEM AND METHOD FOR TISSUE ANALYSIS USING REMOTE PPG

CROSS-REFERENCE TO PRIOR APPLICATIONS

This application is the U.S. National Phase application under 35 U.S.C. § 371 of International Application No. PCT/EP2023/053768, filed on Feb. 15, 2023, which claims the benefit of European Patent Application No. 22157397.5, filed on Feb. 18, 2022 and European Patent Application No. 22157421.3, filed on Feb. 18, 2022 and International Application No. PCT/EP2023/052103, filed on Jan. 29, 2023. These applications are hereby incorporated by reference herein.

FIELD OF THE INVENTION

This invention relates to the analysis of tissue using photoplethysmography (PPG) analysis. The invention provides for a processors, systems including such processors, methods and computer programs for implementing the methods on e.g. such processors or systems.

BACKGROUND OF THE INVENTION

Microcirculation is the circulation of the blood in the smallest blood vessels, present in the vasculature embedded within organ tissues. The structure of the microvasculature is extremely complex, as so many capillaries are present in the tissues, with the individual capillaries so convoluted that the blood flow at any given point in any given capillary could be in any direction. For this reason, it can be stated that their overall function becomes averaged. That is, there is an average rate of blood flow through each tissue capillary bed, an average capillary pressure within the capillaries, and an average rate of transfer of substances between the blood of the capillaries and the surrounding interstitial fluid. This is the perfusion of the tissue.

Organ perfusion is a crucial indicator of injury and disease, which may include inflammation, stagnant or stopped blood flow, and all pathologies that can lead to global tissue hypoxia and organ dysfunction. Perfusion monitoring can be used to assess these microvascular injuries and many others, such as the progress of healing of either burned skin or wounds or the recovery of the perfusion downstream of a vessel lesion, and the necrosis (e.g., foot ulceration, sepsis) for patients with diabetes.

Non-contact PPG imaging is a recent emerging technology able of monitoring skin perfusion. PPG imaging utilizes an off-the-shelf camera and a light source to remotely detect the dynamic changes in blood volume beneath the skin and allows extracting blood pulsation signals. PPG imaging allows for the elaboration of large tissue areas, thus building a so-called perfusion map, which is a great advantage with respect to contact PPG. PPG imaging has shown to be capable of detecting skin perfusion perturbations, such as irritation, temperature changes and even flow blockage during pressure measurements and has even been evaluated for peripheral arterial disease assessment.

It is possible to build an amplitude map, that represents the amplitude of the PPG signal per image sensing pixel. Furthermore, it is also possible to build a delay map, which provides a measure of the average time delay between the PPG signal wave of each pixel and a reference PPG signal. There is a small delay in the blood pulsation arrival, due to small differences in the microcirculatory bad, such as the resistance and elasticity of the vessels, as well as different artery branches that supply the recorded tissues.

For the purposes of this application, which relates to processing of non-contact PPG signals, perfusion may be defined as the amplitude of a PPG signal of the tissue, namely the amplitude of the pulsatility extracted from the tissue.

It is well known that the perfusion level is not the same everywhere in the body. For example, in a study by the applicant, PPG imaging of the hands and feet were studied, and it was found that the perfusion level is higher on the palms of the hands rather than on the sole of the feet. This is also true for organs, such as the intestine. The small intestine and the colon have different functions, are far away and are supplied by different artery branches, and accordingly have different perfusion levels.

If different tissue types are present in a single image of a remote PPG camera, a general PPG image analysis will average these differences. For example, if an anastomosis is being performed (e.g. after removal of part of the intestine) and the level of perfusion is measured via PPG imaging, there are different intestines in the image. The image analysis will also not show whether the perfusion difference is physiological or due to a lesion (e.g. ischemia, inflammation).

For example, during open bowel resection, a part of the colon or small intestine is surgically removed to remove a tumor. First, a surgeon mobilizes the bowel from the surrounding organs and membranes. The bowel is clamped on both sides of the tumor and blood flow towards that part is interrupted. The surgeon will then cut out the diseased part of the bowel and stitch the two clamped sides back together, which is called the anastomosis. The intestinal anastomosis is to establish communication between two formerly distant portions of the intestine. This procedure restores intestinal continuity after removal of the pathological condition affecting the bowel. If the anastomosis does not properly heal due to inadequate perfusion, leakages occur. Leakages are dangerous and can lead to severe infections and require hospitalization and reoperation. These leakages occur in 5 to 10% of patients undergoing bowel resection. Here, objective perfusion parameters could help identify inadequate healing.

A PPG signal for an area of interest is obtained by averaging the values of all the pixels for that area for each frame. The resulting average PPG signal can be used to assess the heart rate of the patient, as well as a perfusion level.

For enhancing the strength of the average PPG signal, weighting average methods have been proposed, where the PPG signal of each pixel is weighted with the signal-to-noise ratio (SNR) of the PPG signal. The higher the SNR of the PPG signal of that pixel, the more that pixel contributes to the weighted average.

SUMMARY OF THE INVENTION

The current inventors have recognized that, if a large area of the skin or an organ is recorded, or if far apart areas are recorded simultaneously with a camera, the delay in PPG time arrival influences the average PPG signal. Thus, taking a global average in this case degrades the signal to noise ratio of the signal.

The invention is defined by the claims.

According to examples in accordance with an aspect of the current disclosure, there is provided a system for PPG analysis, comprising a processor adapted to receive images of a region of interest and to process the images to:

determine PPG signals from different image regions of the images;

determine relative delays between the PPG signals for the different image regions;

improve the alignment between the PPG signals in time; and determine a global PPG signal for the overall region of interest by combining the time-adapted PPG signals.

By determining the different delays for different image regions (i.e. image pixels corresponding to image sensor pixels), it is possible to realign or partially realign the PPG signals so that a global signal for the overall region of interest may be obtained with improved signal to noise ratio. The destructive interference caused by averaging PPG signals with different time delays is thereby reduced or avoided. An improved alignment of PPG signals thus may comprise reduction of one or more delays between such signals so that less destructive interference of the signals occurs as compared to the situation without such improved alignment.

The PPG signals may be aligned with corresponding timing (i.e. the PPG signals are perfectly synchronized to a reference signal). However, improved alignment may be achieved as long as the delay between the local PPG signal and a reference PPG signal decreases, the destructive interference caused by averaging PPG signals with different time delays is reduced, and therefore an improvement of the global PPG signal is obtained.

By way of example, the average timing difference compared to a reference PPG signal is reduced to below 50% of its initial value, or below 40%, or below 30%, or below 20%.

In the case of an anastomosis, by averaging the signals from the two different tissue types, e.g. the two ends of the intestine, a smoother PPG signal is found.

The processor is for example adapted to:

derive a reference PPG signal;

determine the relative delays between the PPG signals by determining a delay of each PPG signal relative to the reference PPG signal; and align the PPG signals in time by providing a common delay relative to the reference PPG signal.

Thus, in this case, the PPG signals are time-aligned relative to a reference and hence relative to each other.

The reference PPG signal for example comprises:

an average PPG signal for the region of interest; or an average PPG signal for a portion of the region of interest;

a PPG signal for an individual image region; or a PPG signal from an area of the body outside the region of interest.

The reference PPG signal is in all cases acquired simultaneously with the image sequence of the region of interest.

The relative delays for example comprise a delay relative to a reference PPG signal. The delay is computed as the average time delay between the PPG signal wave of each pixel and the reference PPG signal, over a certain time period.

The length of the time period includes at least a heartbeat cycle and the reference PPG signal is obtained as a spatial average of the all pixel values of a video (or series of images) which is a time-dependent signal modulated at the heart rate. A signal is created which varies over time, frame by frame.

The processor is for example adapted to generate and output a PPG perfusion map.

The remote PPG sensing is thus used to derive a PPG perfusion map from PPG amplitude levels. Remote PPG sensing can thus show perfusion levels at different locations as well as providing an accurate overall perfusion level.

The processor is for example adapted to generate and output a PPG delay map.

The PPG delay map shows relative delays of arrival of the pulsatile blood flow to the tissue. The delay information is for different image regions, i.e. the image data associated with different pixels of the image sensor.

The processor is for example adapted to determine a global PPG signal for the overall region of interest by averaging the aligned PPG signals.

The system may comprise a camera for capturing the images of the region of interest.

The camera may comprise:

a 2D camera or a set of 2D cameras; or a hyperspectral camera or a set of hyperspectral cameras.

The invention also provides a computer-implemented method for processing images to derive remote PPG signals, comprising:

receiving images of a region of interest;

determining PPG signals from different image regions of the images;

determining relative delays between the PPG signals for the different image regions;

improving the alignment between the PPG signals in time; and determining a global PPG signal for the overall region of interest by combining the time-adapted PPG signals.

The method may comprise:

deriving a reference PPG signal;

determining the relative delays between the PPG signals by determining a delay of each PPG signal relative to the reference PPG signal; and aligning the PPG signals in time by providing a common delay relative to the reference PPG signal.

The reference PPG signal may be obtained by:

averaging the PPG signals for the region of interest; or averaging the PPG signals for a portion of the region of interest; or obtaining a PPG signal for an individual image region.

The method may comprise:

deriving a PPG perfusion map based on PPG amplitude levels at the image regions; and/or deriving a PPG delay map based on PPG relative delays between the different image regions.

The method may comprise providing the remote PPG signals or set thereof to a display for output to a user. The method may comprise causing the display to output the remote PPG signals or set thereof to a user. The current disclosure also provides a computer program comprising computer program code means which is adapted, when said program is run on a computer, to implement the method defined above. The computer program may be stored on a computer readable medium such as a non-transient medium. Such medium or media may include memories such as for example described hereinafter. The computer program may be downloadable from a telecommunications network such as 3G, 4G or 5G Network or from an information network such as WAN or LAN network, as known in the art. The computer may be or may comprise the processor as defined herein. The computer may be part of the PPG imaging system. The current disclosure also provides a processor which is programed with the computer program. The processor is for use in the PPG imaging system. The PPG imaging system may be part of a medical imaging system. Such imaging systems may comprise an endoscope or endoscope device or system. These and other aspects of the current disclosure will be apparent from and elucidated with reference to the embodiment(s) and examples described hereinafter.

BRIEF DESCRIPTION OF THE DRAWINGS

For a better understanding of the invention and its aspects, and to show more clearly how it may be carried into effect, reference will now be made, by way of example only, to the accompanying schematic drawings, in which.

DETAILED DESCRIPTION OF THE EMBODIMENTS

Figure 1:
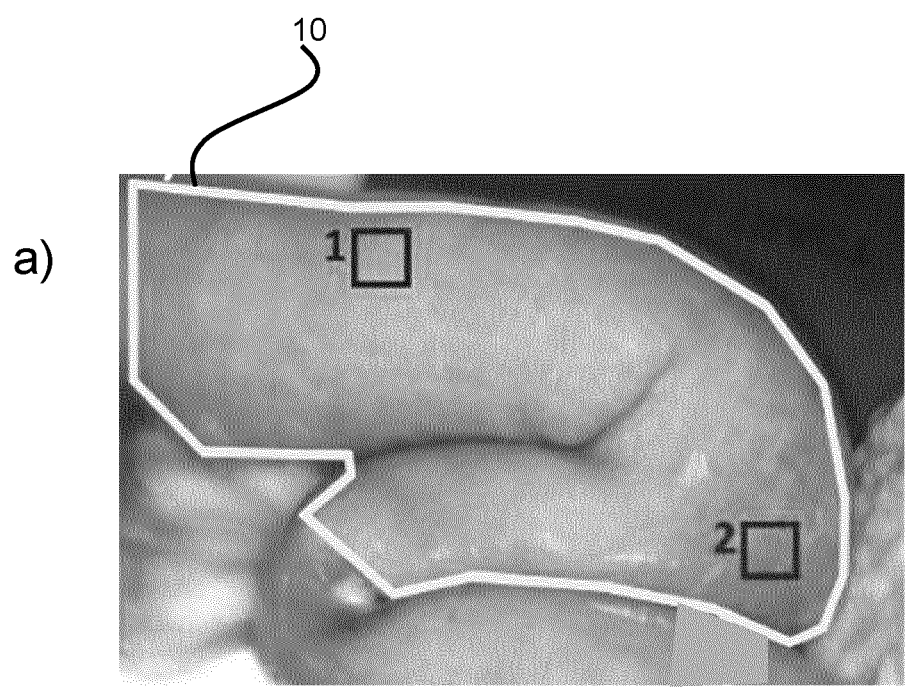
FIG. 1 shows a representation of a frame of a video acquired of the intestine and a global PPG signal derived from the video.
Figure 1:
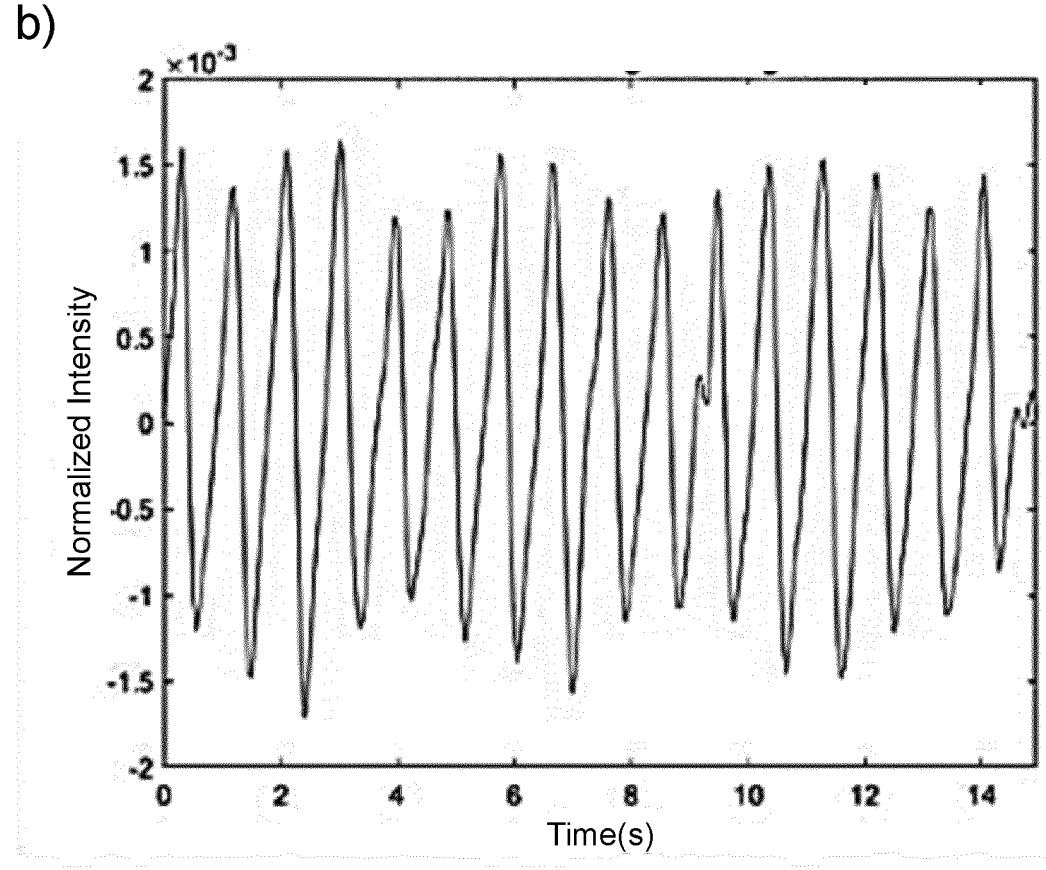

The invention will be described with reference to the examples and Figures.

The detailed description and specific examples, while indicating exemplary embodiments of the systems and methods and computer programs, are intended for purposes of illustration only and are not intended to limit the scope of the claims. These and other features, aspects, and advantages of the apparatus, systems and methods of the present invention will become better understood from the following description, appended claims, and accompanying drawings. The Figures are merely schematic and are not drawn to scale. The same reference numerals are used throughout the Figures to indicate the same or similar parts.

The disclosure provides a system and method for PPG analysis which processes images to determine PPG signals from different image regions of the images and determine relative delays between the PPG signals for the different image regions. The time alignment between the PPG signals is improved so that a more accurate global PPG signal is obtained for the overall region of interest. In this way, PPG signals are realigned or partially realigned to provide an overall PPG signal with improved signal to noise ratio.

Before describing the system and method, the known operation of a remote PPG imaging system, and the known image processing methods, will first be described.

Remote PPG imaging enables a determination of tissue perfusion from images captured of the tissue of interest, e.g. the skin or even tissue beneath the skin. Remote PPG typically uses ambient light, functioning as broad band white light source, and the diffuse and specular reflections are analyzed for different color components. Remote PPG imaging may be used to construct a PPG amplitude map and a PPG delay map.

For this purpose, a camera or a series of cameras (at one or multiple wavelengths) captures video of the tissue area, e.g. skin, at a distance. The measurements derived from the video are remote PPG images, which provide non-contact measurement of a pulse signal by analyzing subtle changes of skin color (or organ color) i.e. at different wavelengths of the light.

It has been proposed to use remote PPG for inflammation detection. It has also been proposed in European Patent Application No. 20214955.5 to measure perfusion based both on a PPG amplitude level and also information about the distribution of the PPG phases, such as a standard deviation or interquartile range of a phase map.

By extracting pulse signals at each individual location of the skin region (corresponding to each pixel of the cameras) a spatial map of the pulse signal can be derived, showing both amplitude and delay. This perfusion map thus represents the amplitude and delay of the PPG signal per pixel and hence per location of the skin.

FIG. 1 (a) shows a representation of a frame of a video acquired of the intestine. By spatial averaging the pixel values in the region of interest (ROI) 10, a signal can be derived from the video, modulated at the heart rate. This signal is shown in FIG. 1 (b) as a normalized intensity of the PPG signal versus time.

The PPG signal of FIG. 1 (b) represents an average for the whole region of interest.

However, separate signals may also be captured from smaller regions of interest, shown as region 1 and region 2 in FIG. 1 (a).

Figure 2:
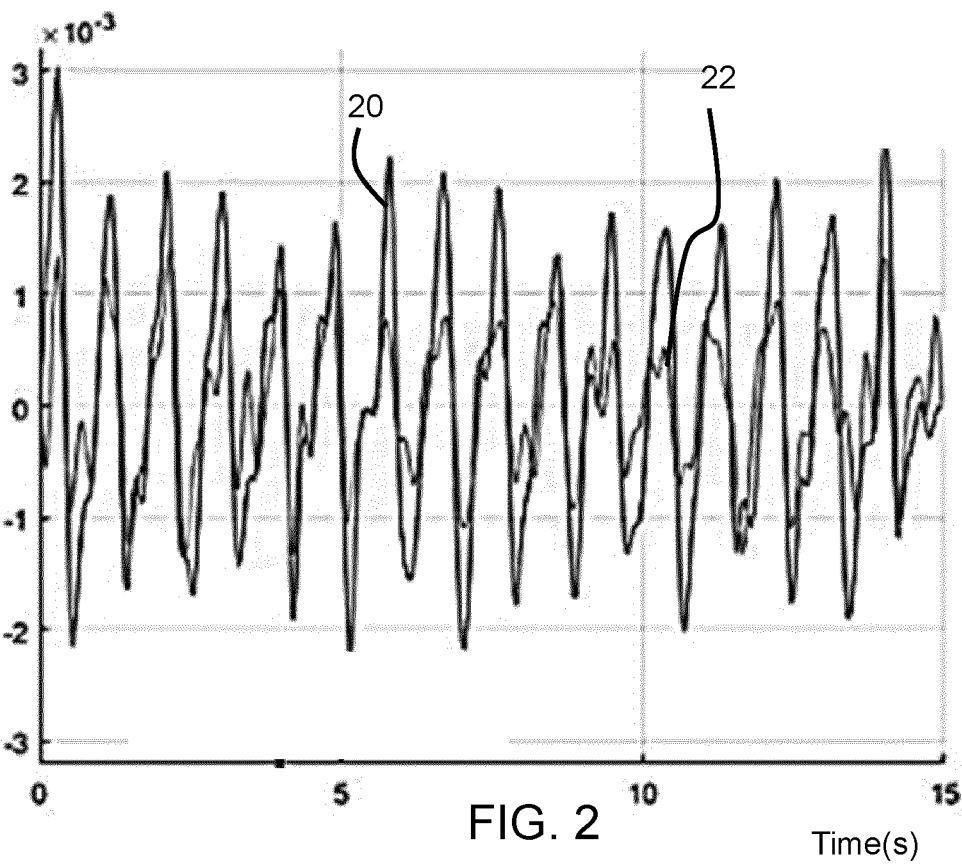
FIG. 2 shows separate PPG signals for separate regions of interest.

FIG. 2 shows separate PPG signals, as a first signal 20 for the first region of interest and a second signal 22 for the second region of interest. The two PPG signals are modulated at the same heart rate frequency, but show a different amplitude. By extracting the amplitude from the PPG signal of each separate region of tissue, i.e. from each corresponding pixel of the captured video, a PPG perfusion map may be obtained, as shown in FIG. 3.

Figure 3:
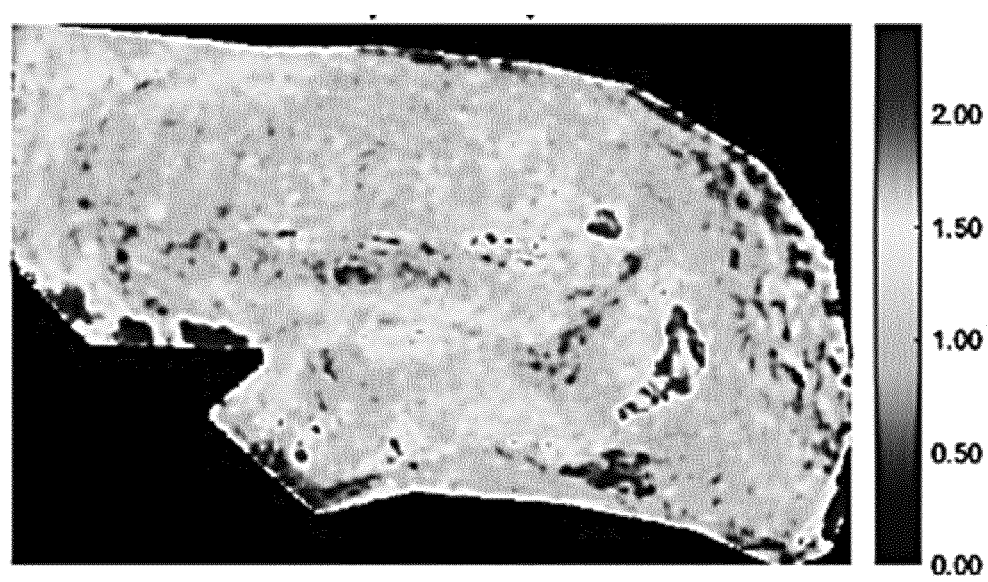
FIG. 3 shows a PPG perfusion map.

FIG. 3 is a black and white representation. However, the PPG perfusion may be color-coded, for example assigning a more red color to areas with higher perfusion and a more blue color to areas with lower perfusion. The PPG amplitude map thus represents the amplitude of the PPG signal per pixel and hence per location of the skin or other tissue being analyzed.

Additional valuable information may be obtained by analyzing the PPG signals.

Figure 4:
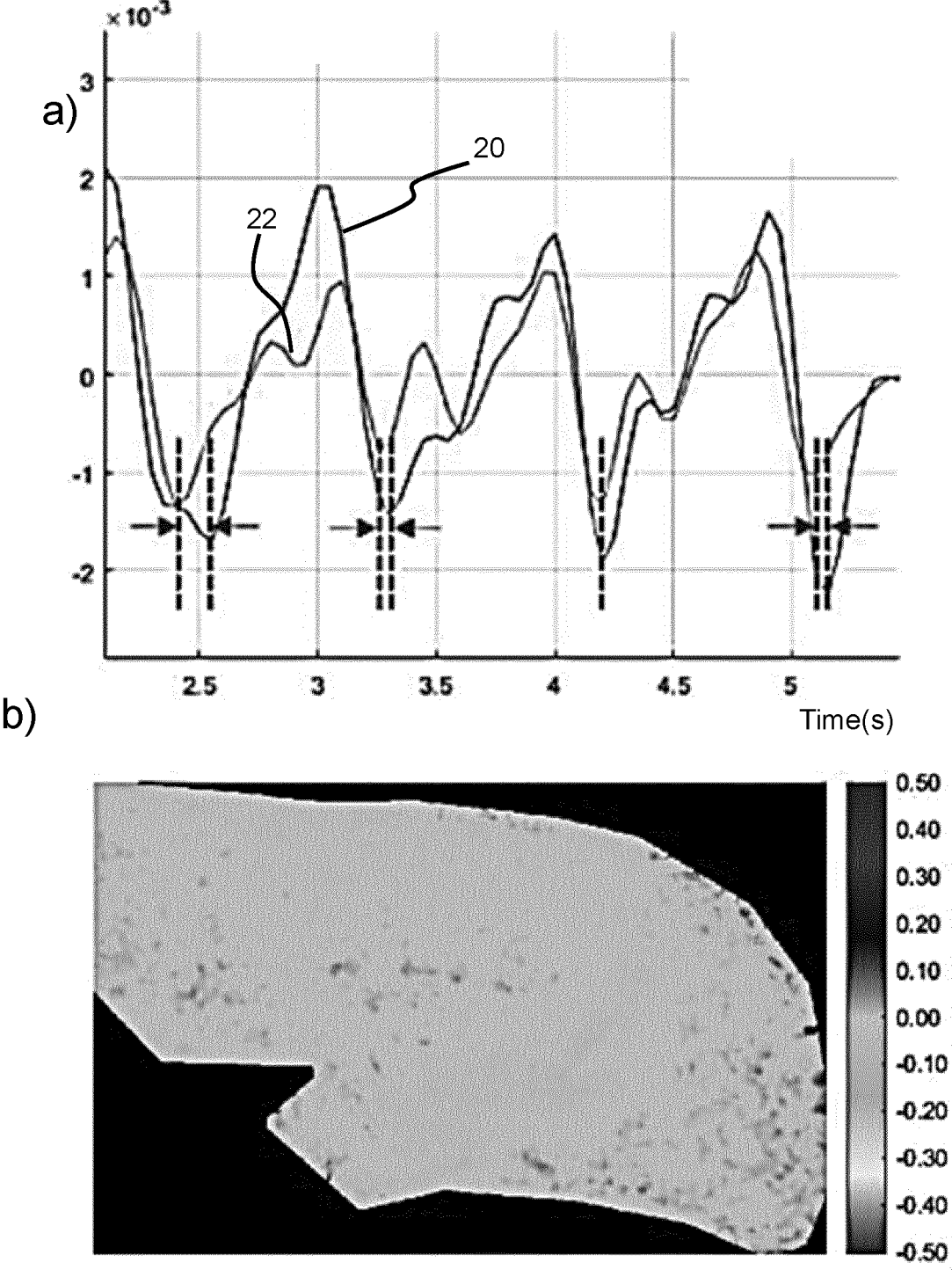
FIG. 4 shows a zoom-in of the PPG signals extracted from the two regions of interest from FIG. 2 and a PPG delay map.

FIG. 4 (a) shows a zoom-in of the PPG signals extracted from the two regions of interest from FIG. 2. Even though the signals are extracted simultaneously from the same organ, the pulsation arrives slightly before in one area than in the other. There is a small delay in the blood pulsation arrival, due to small differences in the microcirculatory bed, such as the resistance and elasticity of the vessels, as well as different artery branches that supply the recorded tissues.

The delays of the PPG signals of each pixel with respect to a reference signal may be extracted and used for building a delay map. The delay map is shown in FIG. 4.

Since the delay between the signals is not always constant but varies during the acquisition, an average delay is used between signals per pixel.

The average delay represents the average time delay between the PPG signal of each pixel and a reference PPG signal. In this way a signal in time is built. The length of the PPG signal should include at least a heartbeat cycle, so it is subject dependent.

The average delay is a value of delay assigned to each pixel. From the plot of FIG. 4, it can be seen that there is a difference in time arrival between the peaks of the PPG signals. Therefore, for each pixel, the average of these delay (with respect to a reference signal) is assigned. At the end, the delay map is built, where each pixel contains the average delay between the PPG signal of that pixel and the reference PPG signal.

By acquiring a video stream, a series of images is obtained over time, for example with a frame rate of 20 frames per second. To compute the global PPG signal over time, the pixel values of the frame 1 are spatially averaged, so that the 2D set of pixels yields one value. The pixels of frame 2 are then averaged, and so on.

Eventually, a PPG signal is obtained over time (with the same length as the video that has been acquired), where each value of the signal is a spatial average of one corresponding frame of the video acquired. The image frames for example comprise 968×728 pixels, by way of example.

The PPG signal of each pixel is thus compared with the global PPG signal being used as a reference. The value assigned to each pixel "n" of the delay map thus represents the average delay between the PPG signal in the pixel "n" and the global PPG signal being used as a reference. Thus, the value of the delay for each pixel in the PPG delay map represents the average delay (in terms of average time shift) between the PPG signal of that pixel and the global PPG signal. The delays are for example computed by using the lock-in amplification algorithm.

The delay map thereby provides a measure of the average time delay between the PPG signal wave of each pixel and the reference PPG signal for at least one heartbeat cycle. The reference PPG signal is the global PPG signal of FIG. 1 (b) extracted from the entire region on interest of the intestine.

Since the reference signal is extracted from the entire region of interest, a PPG signal from a given location of the image is likely to be in phase with the reference.

Similar to the map of the amplitude, FIG. 4 (b) is a black and white representation. However, the PPG delay map may be color-coded. The Hue, Saturation, Value (HSV) color system is for example employed, since it works well with the periodicity of the PPG signal.

For extracting the amplitude maps and delay maps, a lock-in amplification method may be used.

Details on how to calculate the PPG maps using the lock-in amplification method can be found in:
(i) Lai M, Shan C, Ciuhu-Pijlman C, Izamis M L. Perfusion monitoring by contactless photoplethysmography imaging, 2019 IEEE 16th International Symposium on Biomedical Imaging (ISBI 2019) 2019 Apr. 8 (pp. 1778-1782). IEEE; and
(ii) Lai M, Dicorato C S, de Wild M, Verbakel F, Shulepov S, Groen J, Notten M, Lucassen G, van Sambeek M R, Hendriks B H. Evaluation of a non-contact Photo-Plethysmographic Imaging (iPPG) system for peripheral arterial disease assessment, Medical Imaging 2021: Biomedical Applications in Molecular, Structural, and Functional Imaging 2021 Feb. 15 (Vol. 11600, p. 116000F). International Society for Optics and Photonics.

Because of the great advantages that the remote PPG technology has shown for remotely and non-invasively assessing skin-level perfusion, PPG imaging can be translated to organ perfusion assessment for detecting the perfusion of the microvasculature tissue bed beneath the organ surface, without any modification to the current acquisition setup.

Figure 5:
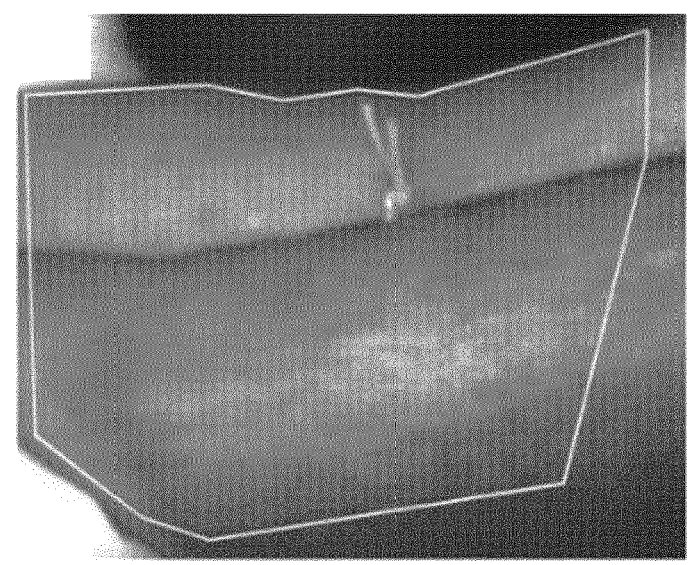
FIG. 5 shows an image of an intestinal area after open bowl resection, the corresponding amplitude map and the corresponding delay map.
Figure 5:
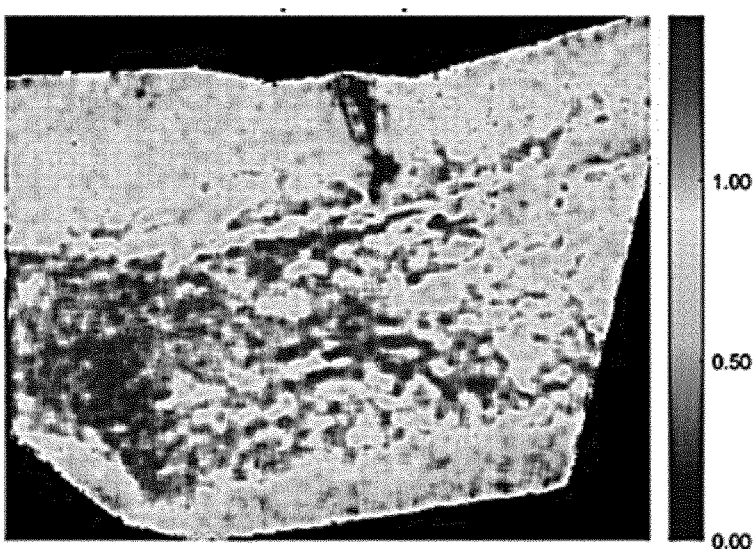
Figure 5:
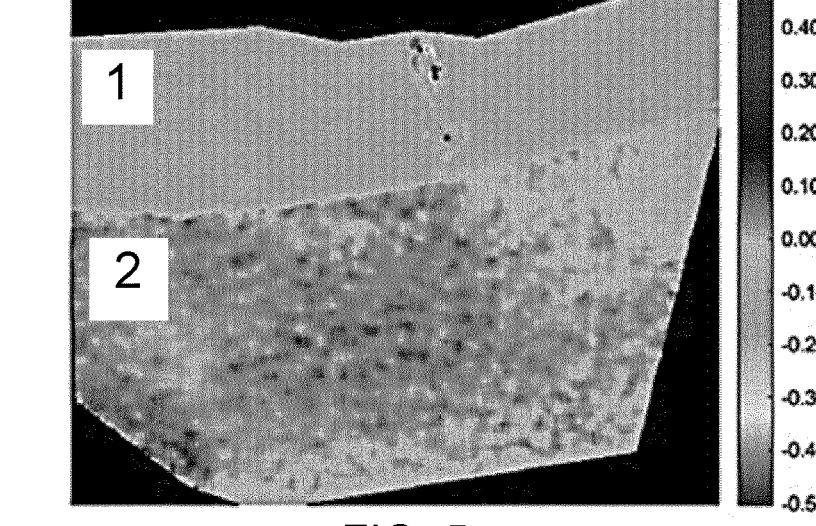

FIG. 5 (a) shows an image of an intestinal area after open bowl resection. FIG. 5 (b) shows the corresponding amplitude map (normalized with respect to the maximum value) and FIG. 5 (c) shows the corresponding delay map.

The delay map clearly shows that there are two areas which each have a relatively uniform delay value but they are different to each other (in color, the two images are predominantly different colors, such as blue and green).

The areas are supplied by different arterial branches and there is a relative difference in the PPG time arrival between the areas. This could be assessed by comparing the PPG signals extracted from the two areas.

Figure 6:
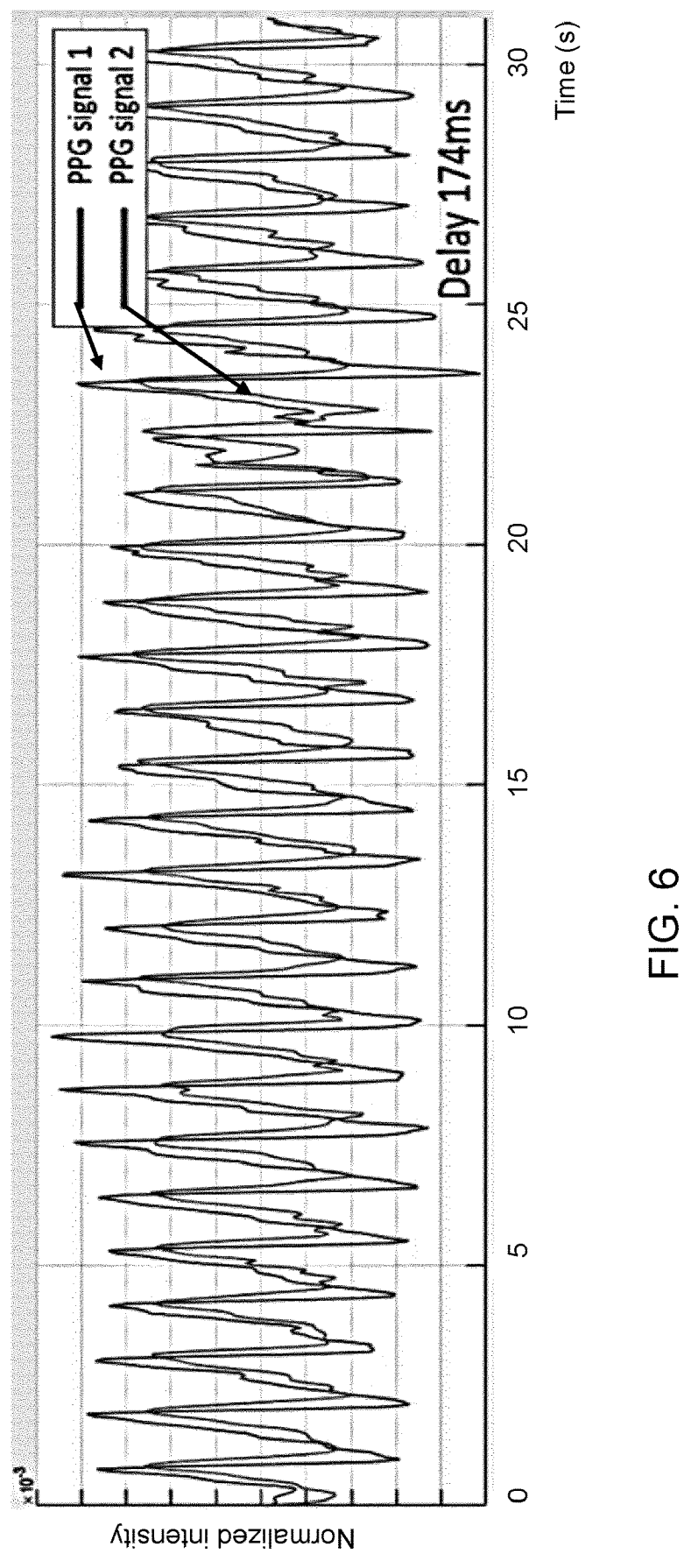
FIG. 6 an average PPG amplitude for each area.

FIG. 6 the average PPG amplitude for each area. The PPG amplitude level is different, but it can also be seen that one PPG signal arrives slightly before the other. The relative delay is 174 ms.

In the case of FIG. 1, the delay between different areas is relatively small and is mainly due to slight changes in vascular resistance and compliance. However, the delay seen in FIG. 6 is dependent on the PPG arrival time in the two areas.

The two areas will each have a spread of different delay times. However each area will have a different average and an associated spread. Thus, ranges of PPG delay times, from the PPG delay map, may be used for classification.

For example, two areas of a PPG delay map may be considered separate if the difference of their delays is larger than a threshold such as 20 ms, preferably more than 50 ms and even more preferred larger than 100 ms.

The approach of the current disclosure is explained with referenced to FIGS. 7 to 11.

Figure 7:
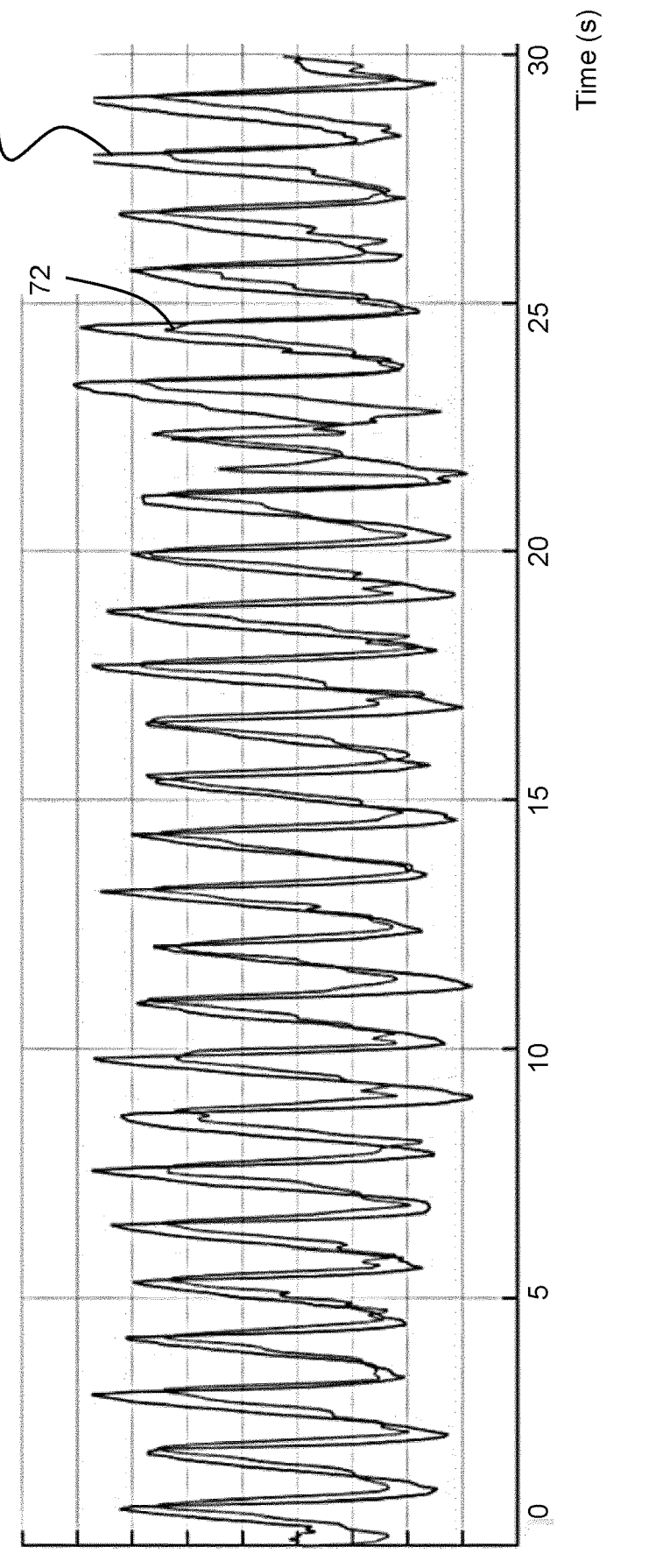
FIG. 7 shows a plot of a reference PPG signal and a plot of a PPG signal from one pixel of the camera image.

FIG. 7 shows a plot 70 of a reference PPG signal and a plot 72 of a PPG signal from one pixel of the camera image.

Figure 8:
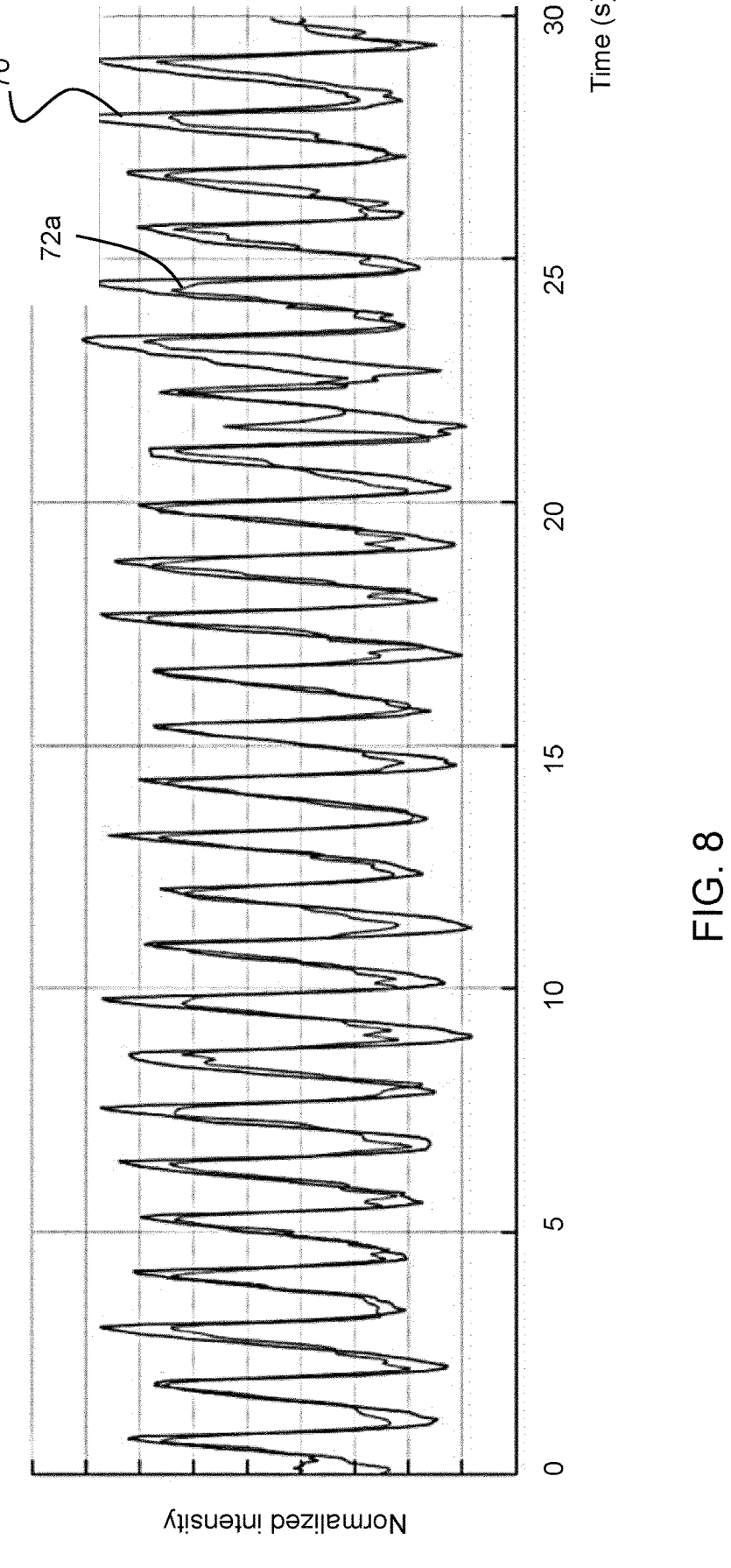
FIG. 8 shows the same plot of a reference PPG signal and a plot of the same PPG pixel signal but synchronized with the reference PPG signal.

FIG. 8 shows the same plot 70 of a reference PPG signal and a plot 72a of the same PPG pixel signal but synchronized with the reference PPG signal.

The reference PPG signal 70 may be computed by averaging the pixel values of the region of interest (ROI) from each frame. The reference signal could instead be the average PPG signal from a portion of the image, or the PPG signal from a single pixel, or even a PPG signal extracted from another area of the body, for example using a contact probe (using standard PPG).

The delay of the PPG signal 72 of each pixel, with respect to the reference signal, is computed so that the synchronization of the PPG signal of each pixel can take place relative to the reference signal as shown in FIG. 8.

In this way, all the synchronized PPG signals of each pixels are averaged, to result in a PPG signal with higher SNR than the simple average of all the pixels PPG signals without synchronization.

Figure 9:
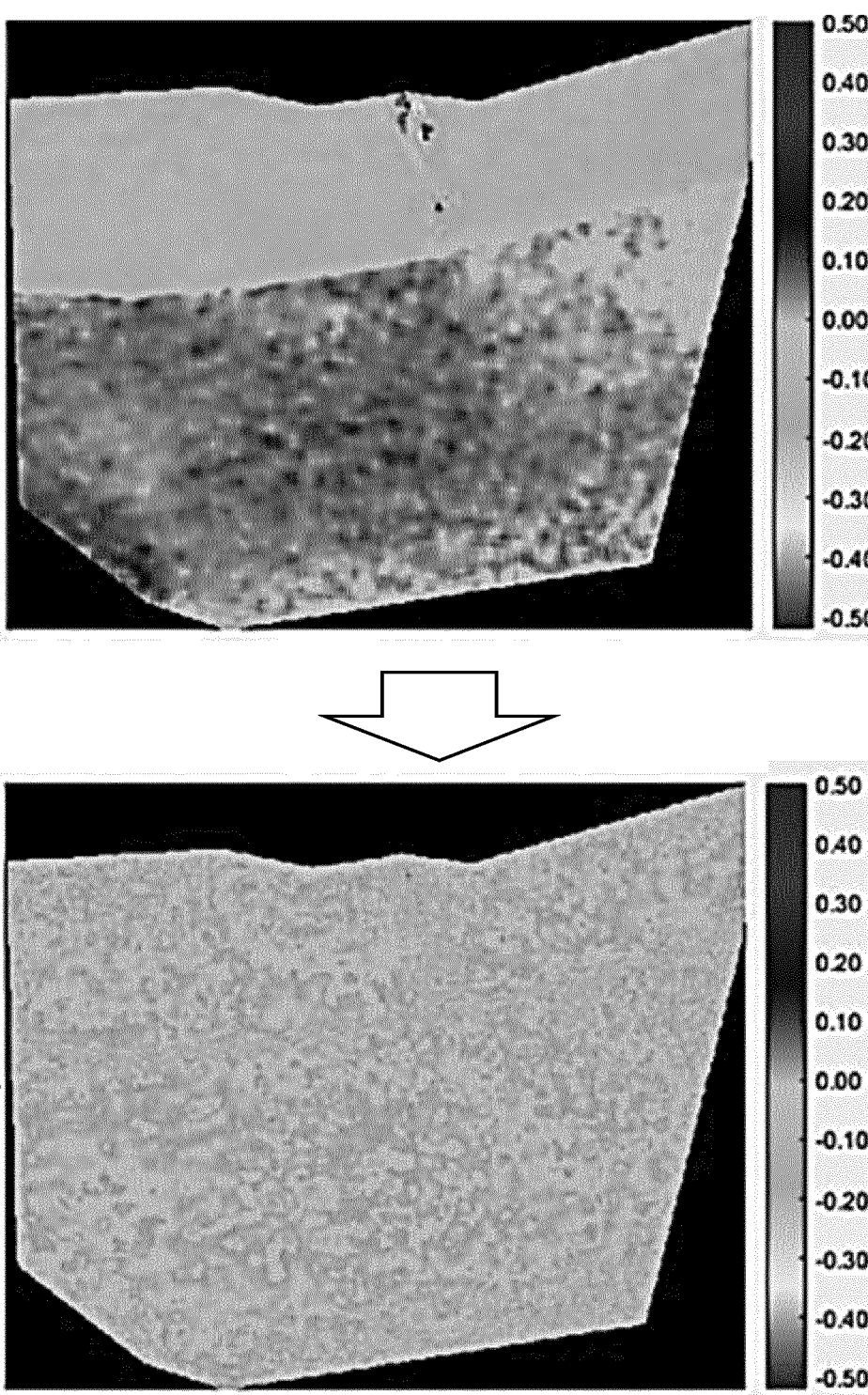
FIG. 9 shows the effect on the delay map of the pixel synchronization.

FIG. 9 shows the effect on the delay map of the pixel synchronization. The top image is a delay map before PPG signal synchronization and the bottom image is a delay map after PPG signal synchronization.

Figure 10:
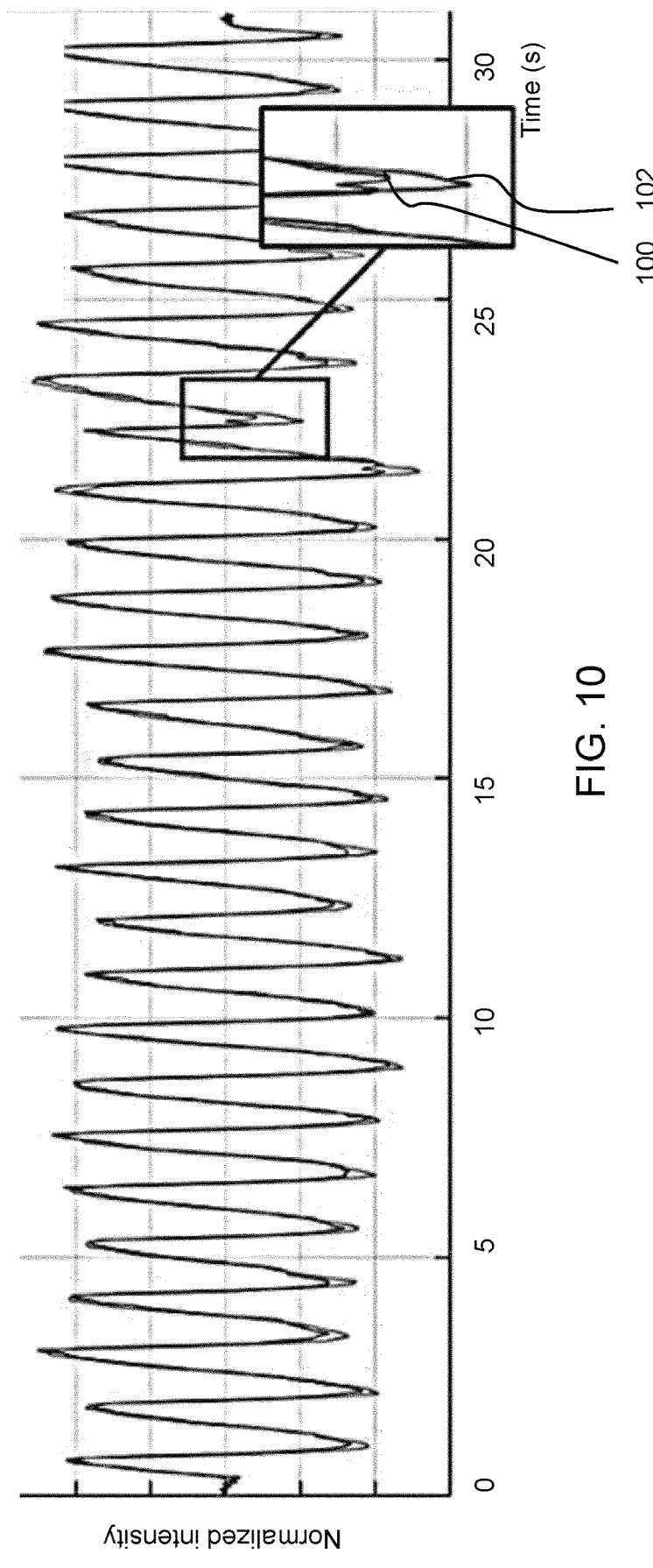
FIG. 10 shows a comparison of the average PPG signal obtained by simply averaging all the PPG signals and the average PPG signal after the PPG signals are synchronized.

FIG. 10 shows a comparison of the average PPG signal 100 obtained by simply averaging all the PPG signals (in this case the average PPG signal is also the reference signal), with respect to the average PPG signal 102 after the PPG signals are synchronized.

The enlarged area in FIG. 10 shows that artifacts in the average signal are reduced.

Figures 11, 12:
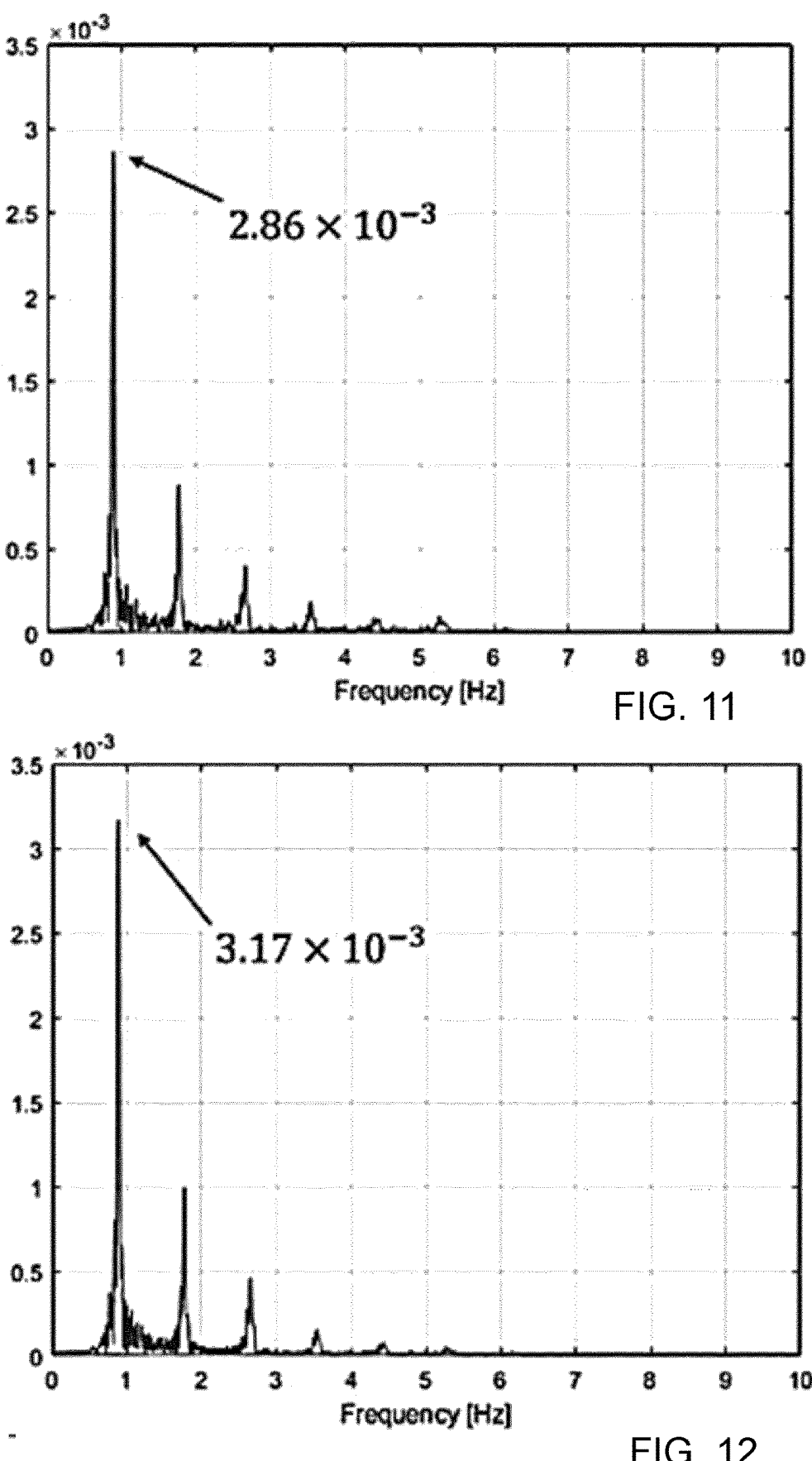
FIG. 11 shows the frequency spectra for the simply averaged PPG signal.
FIG. 12 shows the frequency spectra for the synchronized average PPG signal.

FIG. 11 shows the frequency spectra for the average PPG signal 100 and FIG. 12 shows the frequency spectra for the average PPG signal 102.

The spectra of the two signals show that the synchronized PPG signal peak is higher than the more simple average signal peak. Thus, the signal to noise ratio is increased. This approach enables synchronization of two or more PPG signals from different and far apart areas so that a more accurate general PPG analysis may be performed.

Figure 13:
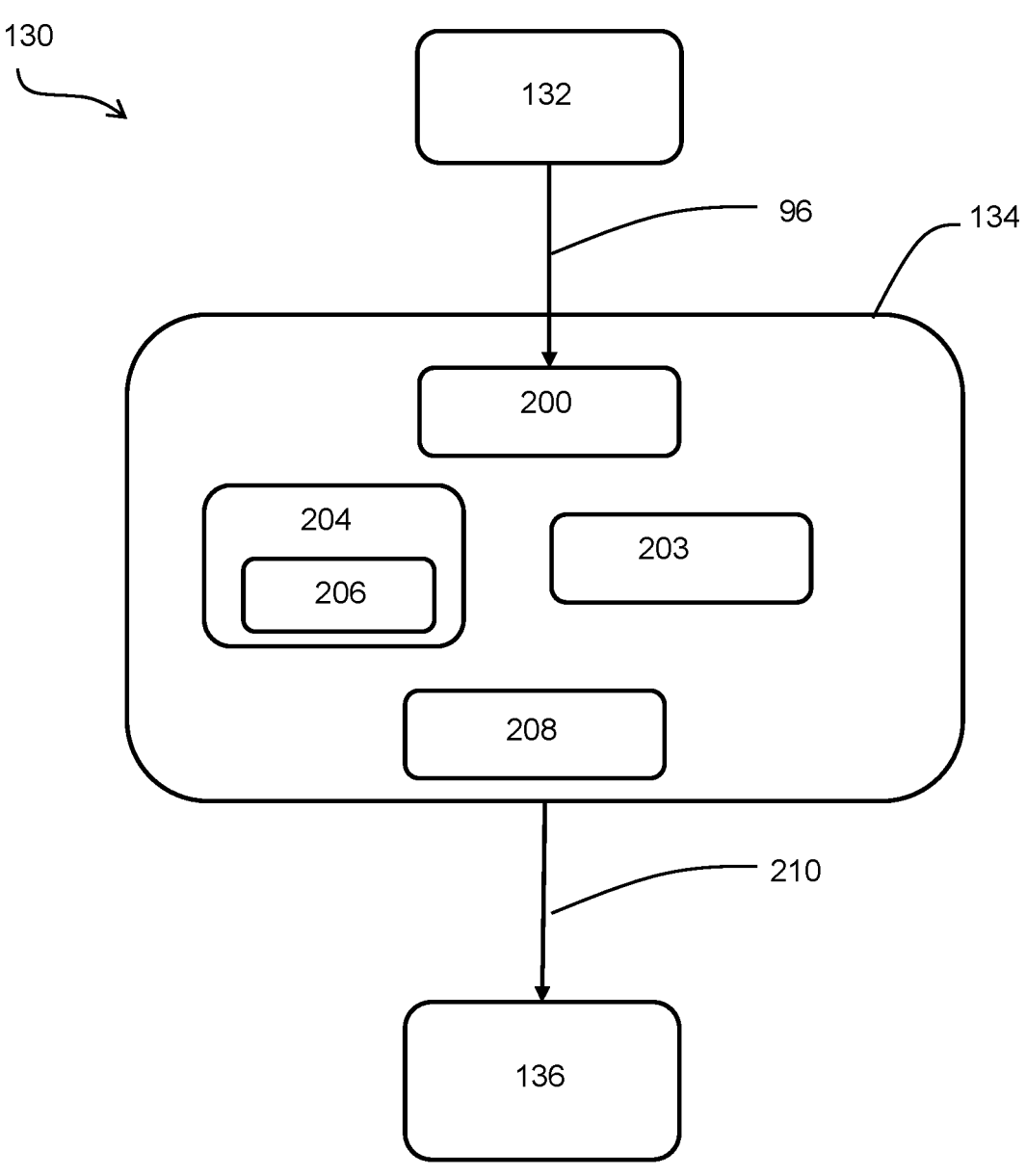
FIG. 13 shows system for tissue analysis.

FIG. 13 shows system 130 for tissue analysis. The system comprises one or more imaging cameras 132. The system also comprises a processor 134 adapted to receive the images (in a passive sense under control of another device) or obtain (in an active sense under its own control and thus causing the receipt) and process the images. The image processing creates a more accurate perfusion measure P.

The processor 134 may include an input 200 for receiving the images via an input signal (that may also be represented by reference numeral 96) either or not as a consequence of a processor generated control signal causing active obtaining of the images from another device such as a camera 132 or repository 132 storing such images. Such input 200 can comprise and/or be based on USB, Firewire, or other type for transmission of images, as known in the art. The input 200 may comprise and/or be based on wireless transmission such as Bluetooth or wifi, as known in the art. Communicative coupling may be wired and/or wireless.

The input 200 may be configured to be, or is, communicatively coupled to an image sensor 132 or image camera 132 such as a 2D- or 3D-image sensor, or a 2D-, or 3D image camera. If appropriate the image sensor may be a 3D image sensor or 3D camera. Alternatively, or additionally the input is configured to be communicatively coupled to a repository for storing images. Such repository may comprise or be memory 202 as described herein below. Images may form part of video.

The processor 134 may be or may comprise a processor circuit. It may have a central processing unit (CPU) 203 one or more memories 204 for storing data 206 used by the processor and/or instructions of computer programs 206 for implementing steps performed by the processor or another computer as defined herein. The processor or processor circuit may include busses as known in the art for communication between different parts such as between the input, output, memory and a data processor. The processor and/or processor circuit may be designed according to known contemporary electronic principles in for example silicon-based technology possibly made using semiconductor manufacturing technology. The memory may be ROM or RAM based. It may be based on electrical storage such as EPROM, FLASH DRAM, SRAM and the like and/or based on optical storage such as with CD, CD-ROM, DVD or Blue Ray or the like and/or it may be based on magnetic storage such as with magnetic hard disk or the like.

The processor or processor circuit may be part of or even take the form of a computer as comprised in a laptop or workstation, tablet or other mobile or stationary device. It may be stand alone or integrated in other devices or systems. The system has a display 136 for displaying the output, for example as a perfusion map and a delay map and/or as PPG signals over time. The processor 134 is or can be communicatively coupled to a display 136 and controls the display 136 to display PPG signals 210, for example as a perfusion map and/or a delay map and/or a set of PPG waveforms. To this end the processor may have an output 208 that can be or is communicatively coupled to the display 136 and is capable of outputting the set of PPG signals 210 using an appropriate signal 210. Such output can comprise or be based on VGA, Display port, HDMI, USB or other. The output may be based on wireless transmission such as Blue tooth or wifi as known in the art The tissue classification may use machine learning algorithms, such as Support Vector Machines (SVMs) and Convolutional Neural Networks (CNNs).

The field of view of the camera could include all of the organs inside the abdomen or only a part of the organs inside. By classifying the tissue types present in the field of view, a comparison of perfusion is prevented between tissues which can have different levels of perfusion due to their different functions. These different tissues can even be supplied by different artery branches.

Figure 14:
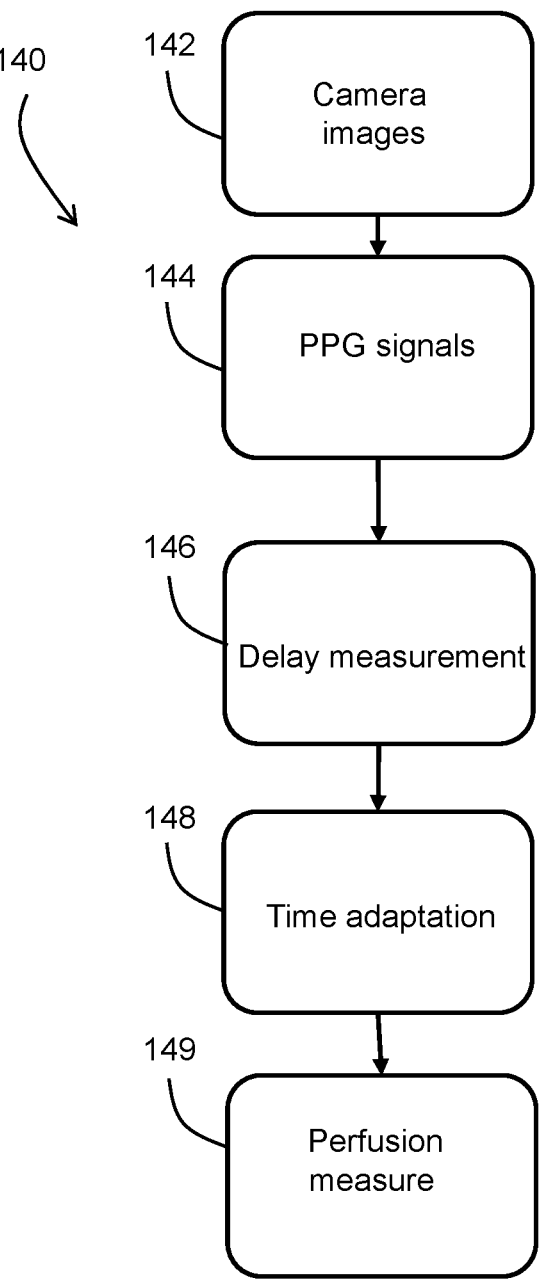
FIG. 14 shows a method for tissue analysis.

FIG. 14 shows a computer-implemented tissue analysis method 140. The method 140 comprises receiving image sensor images in step 142.

PPG signals are determined in step 144 from different image regions of the images.

Relative delays between the PPG signals for the different image regions are determined in step 146, and the signals are adapted in step 148 to improve the alignment between the PPG signals in time. A global PPG signal for the overall region of interest is then obtained in step 149 by combining the time-adapted PPG signals and hence enabling a perfusion measure to be obtained.

The remote PPG sensing used in the system and method described above may be performed using broad band illumination, such as using ambient light and visible light cameras.

However, there is also the option of using hyperspectral imaging. Hyperspectral imaging (HSI) is an emerging imaging modality for medical applications that offers great potential for non-invasive disease diagnosis and surgical guidance. The objective of hyperspectral imaging is to collect a three-dimensional dataset of spatial and spectral information, known as hypercube.

Figure 15:
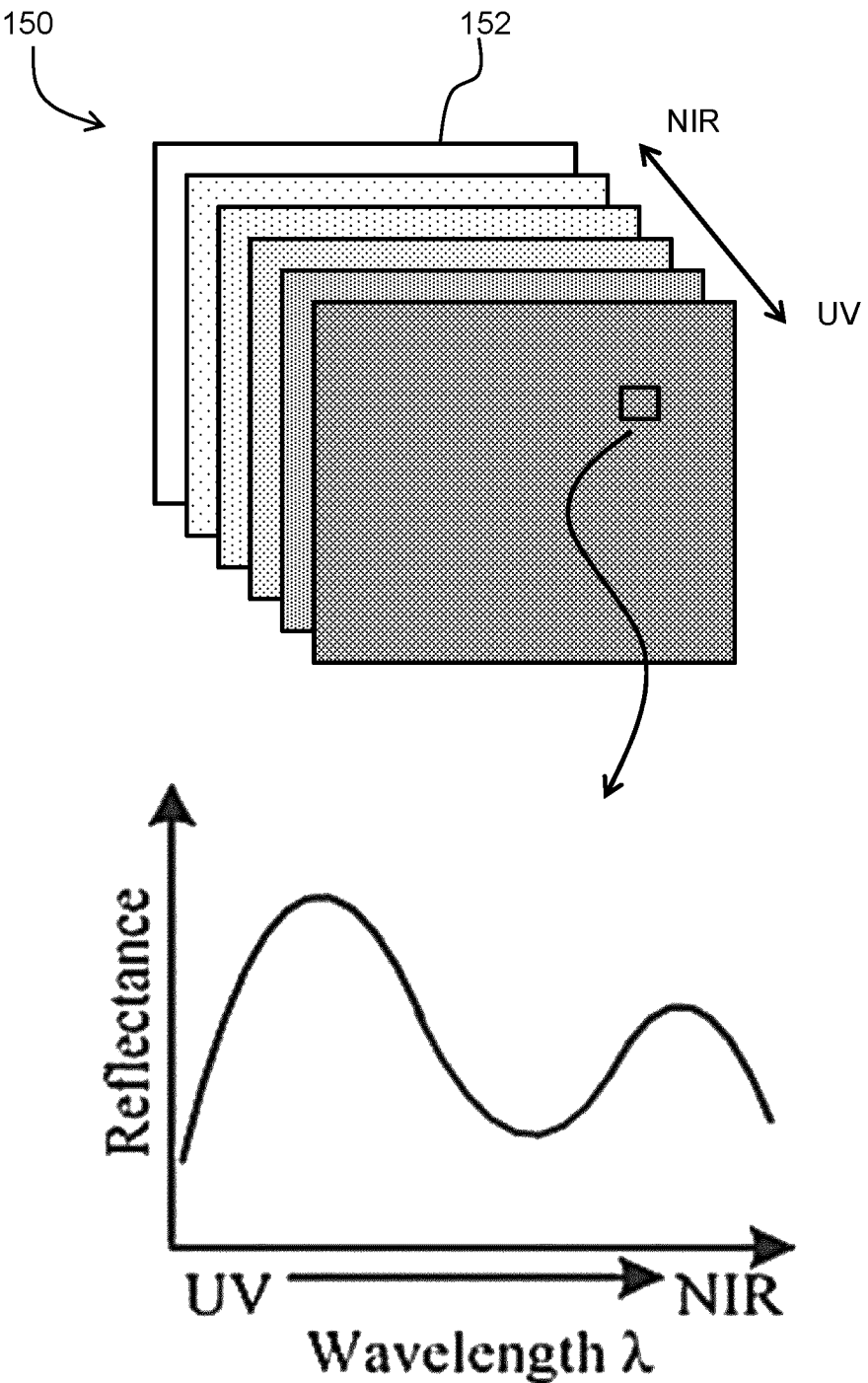
FIG. 15 shows a hypercube of a hyperspectral camera.

As shown in FIG. 15, the hypercube is three-dimensional dataset 150 comprising two-dimensional images 152 at each of a set of wavelengths. FIG. 15 also shows a reflectance curve (i.e. the spectral signature) of a pixel in each image.

The use of hyperspectral images allows additional image processing to be performed, for example it enables a level of oxygenation of tissue to be obtained. A contact PPG probe contains two LEDs and photodetectors at two different wavelengths. By combining the readings at these two wavelengths, an estimation of the oxygen level is possible. For non-contact PPG, RGB cameras have red, green, and blue channels but they are sensitive to much broader wavelength ranges, so extracting oxygenation from a normal RGB camera is not possible. The HSI camera acquires images at specific and narrow wavelengths, so the images can be combined to extract oxygenation values.

The use of hyperspectral images allows additional image processing to be performed, for example it enables a level of oxygenation of tissue to be obtained.

Variations to the disclosed embodiments can be understood and effected by those skilled in the art in practicing the claimed current disclosure, from a study of the drawings, the disclosure and the appended claims. In the claims, the word "comprising" does not exclude other elements or steps, and the indefinite article "a" or "an" does not exclude a plurality.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to". If the term "arrangement" is used in the claims or description, it is noted the term "arrangement" is intended to be equivalent to the term "system", and vice versa.

Any reference signs in the claims should not be construed as limiting the scope.

The invention claimed is:

1. A system, comprising a processor adapted to:
   receive a plurality of (photoplethysmography) PPG signals, each associated with an from different image regions in a region of interest;
   derive a reference signal from the PPG signals;
   for each signal of the PPG signals, determine a delay for the signal relative to the reference signal;
   align each signal of the PPG signals by the delay; and
   determine a global PPG signal for the region of interest from the PPG signals which have been aligned.

2. The system of claim 1, wherein the reference PPG signal comprises:
   an average of the PPG signals for the region of interest;
   an average of a subset of the PPG signals associated with a portion of the region of interest;
   a PPG signal associated with an individual image region; or
   a PPG signal from an area outside the overall region of interest.

3. The system of claim 1, wherein the processor to realign each signal of the PPG signals by the delay is further adapted to:
   realign each signal of the PPG signals by an average delay, wherein the average delay is an average of the delays of each signal of the PPG signals relative to the reference signal.

4. The system of claim 1, wherein the processor is adapted to generate and output a PPG perfusion map.

5. The system of claim 1, wherein the processor is adapted to generate and output a PPG delay map.

6. The system of claim 1, further comprising a camera for capturing the images of the region of interest.

7. The system of claim 6, wherein the camera comprises:
   a 2D camera or a set of 2D cameras; or
   a hyperspectral camera or a set of hyperspectral cameras.

8. A computer-implemented method for processing images to derive remote (photoplethysmography) PPG signals, comprising:

receiving images of a region of interest;
   determining PPG signals from different image regions of the images;
   deriving a reference signal from the PPG signals;
   for each signal of the PPG signals, determining a delay for the signal relative to the reference signal;
   align each signal of the PPG signals by the delay; and
   determining a global PPG signal for the region of interest by from the PPG signals which have been aligned.

9. The method of claim 8, comprising obtaining the reference PPG signal by:
   averaging the PPG signals for the region of interest; or
   averaging the PPG signals for a portion of the region of interest; or
   obtaining a PPG signal for an individual image region.

10. The method of claim 8, comprising:
   deriving a PPG perfusion map based on PPG amplitude levels at the image regions; and/or
   deriving a PPG delay map based on PPG relative delays between the different image regions.

11. A non-transitory computer-readable storage medium having stored a computer program comprising instructions to perform a method comprising:
   receiving images of a region of interest;
   determining (photoplethysmography) PPG signals from different image regions of the images;
   deriving a reference signal from the PPG signals;
   for each signal of the PPG signals, determining a delay for the signal relative to the reference signal;
   align each signal of the PPG signals by the delay;; and
   determining a global PPG signal for the region of interest by from the PPG signals which have been aligned.

12. A processor configured to:
   receive a plurality of (photoplethysmography) PPG signals, each associated with an image region in a region of interest;
   derive a reference signal from the PPG signals;
   for each signal of the PPG signals, determine a delay for the signal relative to the reference signal;
   align each signal of the PPG signals by the delay; and
   determine a global PPG signal for the region of interest from the PPG signals which have been aligned.

13. The system of claim 1, wherein the processor adapted to receive the plurality of PPG signals is adapted to:
   acquire a video stream comprising of a series of image frames obtained over time; and
   obtain a PPG signal over time by spatially averaging pixel values of an image frame of the video stream, wherein each value of the PPG signal is a spatial average of a corresponding image frame, and the PPG signal is of a same length of the vide stream.

14. The method of claim 8, wherein the determining the PPG signals from different image regions of the images comprises:
   acquiring a video stream comprising of a series of image frames obtained over time; and
   obtaining a PPG signal over time by spatially averaging pixel values of an image frame of the video stream, wherein each value of the PPG signal is a spatial average of a corresponding image frame, and the PPG signal is of a same length of the vide stream.

* * * * *